United States Patent [19]

Nishida et al.

[11] 3,981,930

[45] Sept. 21, 1976

[54] DIACETYLENE DIOL DERIVATIVES AND PROCESS FOR PREPARING THE SAME

[75] Inventors: Takashi Nishida; Yoichi Ninagawa, both of Kurashiki; Yoshiaki Omura, Okayama; Fumio Mori; Yoshin Tamai, both of Kurashiki; Takeo Hosogai, Okayama; Yoshiji Fujita; Kazuo Itoi, both of Kurashiki, all of Japan

[73] Assignee: Kuraray Co., Ltd., Okayama, Japan

[22] Filed: May 1, 1975

[21] Appl. No.: 573,569

Related U.S. Application Data

[62] Division of Ser. No. 448,700, March 6, 1974, Pat. No. 3,923,918.

[30] Foreign Application Priority Data

Mar. 19, 1973 Japan.............................. 48-32274
Jan. 14, 1974 Japan................................ 49-7268
Jan. 14, 1974 Japan................................ 49-7269

[52] U.S. Cl............................ 260/635 Y; 260/594; 260/602; 260/615 R; 260/633; 260/635 R; 260/635 M; 260/637 R; 260/638 Y; 260/676 R; 260/682

[51] Int. Cl.$^2$......................................... C07C 33/04

[58] Field of Search................................. 260/635 Y

[56] References Cited
UNITED STATES PATENTS
2,942,014   6/1960   Cameron ....................... 260/635 Y FOREIGN PATENTS OR APPLICATIONS
1,031,075   5/1966   United Kingdom............. 260/635 Y

OTHER PUBLICATIONS

Faulkner, et al., "J. Am. Chem. Soc.", vol. 95 (1973), pp. 553–563, QD1A5.
Slezak et al., "Chem. Abst.", vol. 56 (1962), columns 7131–7132, QD1A51.

*Primary Examiner*—Joseph E. Evans
*Attorney, Agent, or Firm*—Flynn & Frishauf

[57] ABSTRACT

Novel 2,6,10,15,19,23-hexamethyltetracosa-11,13-diin-10,15-diol derivatives. Such derivatives are prepared by oxydative coupling of 3,7,11-trimethyldodeca-1-in-3-ol derivatives or by ethynylation of 6,10-dimethylundecan-2-on derivatives with diacetylene and used as starting materials for preparing squalane.

6 Claims, No Drawings

DIACETYLENE DIOL DERIVATIVES AND PROCESS FOR PREPARING THE SAME

This is a division of application Ser. No. 448,700, filed Mar. 6, 1974 now U.S. Pat. No. 3,923,918.

This invention relates to methods for the industrial preparation of squalane. More particularly, this invention relates to new intermediates for preparing squalane and new methods for preparing the same and squalane.

The intermediates according to this invention have the following formula (I):

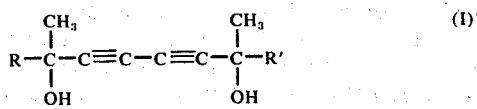

wherein R and R' are the same or different and represent saturated or unsaturated hydrocarbon residues having 11 carbon atoms represented by the following carbon atom skeleton:

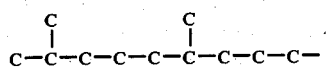

and may be substituted by radicals capable of being replaced by hydrogen atoms upon hydrogenolysis.

According to this invention, the intermediates (I) can be prepared by the following methods:

a. a reaction of $C_{15}$-ketone having 13 carbon atoms represented by the following formula (II)(hereinafter referred to as $C_{13}$-ketone) or its mixture:

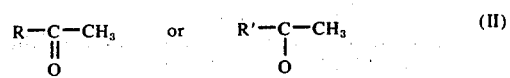

wherein R and R' are the same as above with diacetylene according to the usual method.

b. an oxydative coupling method of a monoacetylene alcohol represented by the following formula (III) or its mixture (hereinafter referred to as monoacetylene alcohol):

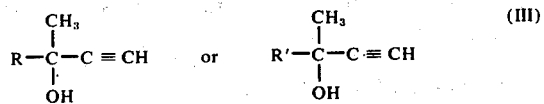

wherein R and R' are the same as above by the usual method.

According to this invention, squalane can be prepared by the following methods using the intermediates (I) as starting materials:

c. a hydrogenolysis method of the intermediates (I)
d. a method which comprises hydrogenation of the intermediates (I) to give the unsaturated compounds having the same carbon skeleton as the intermediate and having hydroxy radicals but no triple bonds and then submitting the above resultant to hydrogenolysis.

An object of this invention is to provide a industrial preparation of squalane.

A further object of this invention is to obtain squalane in low costs and industrial scale.

Another object of this invention is to provide the new intermediates (I) for preparing squalane.

A still further object of this invention is to provide methods for preparing the intermediates (I).

A particular object of this invention is to provide methods for preparing the intermediates (I) using usual available substances as starting materials by the usual method.

All other objects of this invention will in part be obvious from the contents of the specification hereinafter disclosed.

As is known, squalane, 2,6,10,15,19,23-hexamethyltetracosane is used as additive or base of several cosmetics because of its characteristics of cleaning action for skin and its penetrating action to skin. Also it is a useful material as lubricant for precision machines. It has now been prepared by hydrogenation of the squalane portion obtained from shark's liver oil; its preparation using industrial products as starting material has never been almost tried. A method for preparing hydrocarbons having about 30 carbon atoms from low polymer product of isoprene has been proposed; but this method gives several isomers having different skeletons and a mixture of products having different molecular weight; even if this mixture contains squalane, it is impossible to separate squalane from it.

According to this invention, squalane can be prepared: (c) by hydrogenolysis of the intermediates (I); or (d) by partial hydrogenation and then hydrogenolysis of the intermediates (I). Therefore, the methods for preparing the intermediates (I) will be explained in details at first.

As has been already described, the intermediates have the following formula:

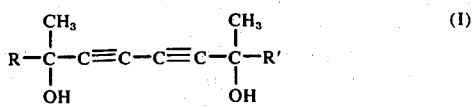

wherein R and R' are the same as above defined.

As radicals capable of being replaced by hydrogen atoms upon hydrogenolysis, R and R' may be substituted by, for example, hydroxy radical, alkoxy radical, oxygen atom ($> = O$), halogen atom (chlorine atom, bromine atom et al), amino radical, imine radical, hydradino radical, nitro radical, thionyl radical, sulfinyl radical, sulfonyl radical and the like. But in view of the industrial preparation, available easiness and costs of starting materials, easiness of the preparation of the compounds (I) or their mixtures and easy transformation of the compounds into squalane, R and R' having no substituent above mentioned may be preferred.

The intermediates (I), as already described, can be prepared: (a) by reacting the $C_{13}$ ketone (II) having the following formula:

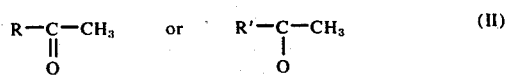

wherein R and R' are the same as above with acetylene; or (b) by coupling a monoacetylene alcohol (III) or its mixture having the following formula:

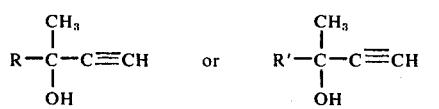

C₁₃ ketone (II) which may be used industrially and usefully are, for example, geranyl acetone, hexahydropseudoionone, 6,10-dimethylundeca-5,11-dien-2-one, pseudoionone, citronellidene acetone, dihydrocitronellidene acetone et al. These ketones can be prepared in industrial scale and at a comparative low price by the following method. For example, geranyl acetone can be prepared industrially by Carroll rearrangement reaction of linallol with acetoacetic acid ester. Hexahydropseudoionone can be easily obtained by hydrogenation of geranyl acetone or pseudoionone. 6,10-Dimethylundeca-5,10-dien-2-one can be easily prepared by partial hydrogenation of 3,7-dimethylocta-7-en-1-in-3-ol obtained by the method of W. Hoffmann et al. (Ann. 747 60 (1971)) to 3,7-dimethylocta-1,7-dien-3-ol and then by Carroll rearrangement reaction of the resultant with acetoacetic acid ester in the same manner as in linallol. Pseudoianone, citronellidene acetone and dihydrocitronellidene acetone can be prepared respectively by aldol condensation of citral, citronellal and tetrahydrocitral with acetone.

Aldol condensation of hydroxycitronellal or alkoxycitronellal with acetone in place of citronellal gives corresponding compounds (II). In general, these hydroxy or alkoxy citronellal can be prepared from citronellal itself and these compounds cannot be preferred to citronellal; these compounds result in only an increase in reaction step.

Diacetylene which is reacted with the C₁₃-ketone (II) has never been used usefully and has been thrown away as by-product in acetylene preparation; so it can be available at a low price.

The monoacetylene alcohols (III) can also be prepared by the reaction of the compounds (II) with acetylene by the same method for preparing the compounds (I) which comprises reacting the compounds (II) with diacetylene, which will be described in details hereinafter. By ethynylation of several compounds (II) with acetylene, the corresponding compounds (III) can be prepared. The compounds (III) having several kinds of substituents can be prepared from the compounds (II) having several kinds of substituents. But as above mentioned, using industrially available compounds (II) is preferred. For example 3,7,11-trimethyldodeca-6,10-dien-1-in-3-ol, 3,7,11-trimethyldodeca-6,11-dien-1-in-3-ol and 3,7,11-trimethyldodeca-1-in-3-ol can be easily prepared by ethynylation of geranyl acetone, 6,10-dimethylundeca-5,10-dien-2-on respectively with acetylene. And these compounds are preferred compounds among the compounds (III) according to this invention.

Upon reaction of the compounds (II) with diacetylene, known methods for preparing acetylene alcohols can be applied broadly. The preferred methods according to this invention are as follows: (1) the method of reaction of the compounds (II) with Grignard compounds of diacetylene in such a solvent as diethyl ether which is used in the general Grignard reaction; (2) the method of reaction of the compounds (II) with diacetylide made by passing diacetylene into the liquid ammonia solution made by dissolving alkali metal or alkaline earth metal such as lithium, sodium, potassium or calcium in liquid ammonia; (3) the method of reaction of the compounds (II) with diacetylene in the presence of an alkaline metal in liquid ammonia or in an organic solvent (for example, the reaction of (II) with diacetylene in the presence of potassium hydroxide or sodium amide and the like in such a solvent as ether or tetrahydrofuran).

Upon oxydative coupling reaction of the compounds (III), known oxydative coupling reaction can be applied broadly. The preferred methods according to this invention are as follows: (4) the method comprising adding a solution of the compound (III) in such a solvent soluble in water or ethanol, acetone or tetrahydrofuran to an aqueous solution of monovalent copper salt such as cuprous chloride and ammonium chloride and oxydative coupling of the compound (III) in an oxygen atmosphere; (5) the method comprising adding the compound (III) to a solution of a monovalent copper salt such as cuprous chloride in a solvent such as pyridine or picoline and oxydative coupling of the compound in an oxygen atmosphere; (6) the method comprising adding the compound (III) to a solution of bivalent copper salt such as cupric acetate in a solvent such as pyridine or picoline.

In the above method (4), a small amount of hydrochloric acid, cupric chloride or ammonia may be added to this system for promotion of the reaction. Also in the above method (6), a reaction promoting agent such as tetramethylethylenediamine may be added and a mixture of pyridine with methanol, ether or acetone may be used.

Representatives of the compounds having formula (I) according to this invention are as follows:
1. 2,6,10,15,19,23-hexamethyltetracosa-2,6,18,22-tetraene-11,13-diin-10,15-diol
2. 2,6,10,15,19,23-hexamethyltetracosa-18,22-diene-11,13-diin-10,15-diol
3. 2,6,10,15,19,23-hexamethyltetracosa-1,6,18,22-tetraene-11,13-diin-10,15-diol
4. 2,6,10,15,19,23-hexamethyltetracosa-2,6,8,18,22-pentaene-11,13-diin-10,15-diol
5. 2,6,10,15,19,23-hexamethyltetracosa-2,8,18,22-tetraene-11,13-diin-10,15-diol
6. 2,6,10,15,19,23-hexamethyltetracosa-8,18,22-triene-11,13-diin-10,15-diol
7. 2,6,10,15,19,23-hexamethyltetracosa-11,13-diin-10,15-diol
8. 2,6,10,15,19,23-hexamethyltetracosa-1,6-diene-11,13-diin-10,15-diol
9. 2,6,10,15,19,23-hexamethyltetracosa-2,6,8-triene-11,13-diin-10,15-diol
10. 2,6,10,15,19,25-hexamethyltetracosa-2,8-diene-11,13 -diin-10,15-diol
11. 2,6,10,15,19,23-hexamethyltetracosa-8-ene-11,13-diin-10,15-diol
12. 2,6,10,15,19,23-hexamethyltetracosa-1,6,18,23-tetraene-11,13-diin-10,15-diol
13. 2,6,10,15,19,23-hexamethyltetracosa-2,6,8,18,23-pentaene-11,13-diin-10,15-diol
14. 2,6,10,15,19,23-hexamethyltetracosa-2,8,18,23-tetraene-11,13-diin-10,15-diol
15. 2,6,10,15,19,23-hexamethyltetracosa-8,18,23-triene-11,13-diin-10,15-diol
16. 2,6,10,15,19,23-hexamethyltetracosa-2,6,8,16,18,22-hexaene-11,13-diin-10,15-diol
17. 2,6,10,15,19,23-hexamethyltetracosa-2,8,16,18-pentaene-11,13-diin-10,15-diol 18. 2,6,10,15,19,23-hexamethyltetracosa-8,18,22-tetraene-11,13-diin-10,15-diol
19. 2,6,10,15,19,23-hexamethyltetracosa-2,8,16,22-tetraene-11,13-diin-10,15-diol
20. 2,6,10,15,19,23-hexamethyltetracosa-8,16,22-triene-11,13-diin-10,15-diol
21. 2,6,10,15,19,23-hexamethyltetracosa-8,16-diene-11,13-diin-10,15-diol Squalane can be prepared by hydrogenolysis of the compound (I) obtained by the above methods. Hydrogenolysis can be carried out at higher temperatures by adding an acidic material to the usual hydrogenation system.

The catalysts used to hydrogenolysis are metal catalysts such as nickel, palladium, and platinum or these metal compounds or catalysts in which these catalyst components are supported on a suitable carrier. The hydrogenolysis using such catalysts can be carried out, for example, by the following methods:

7. the method being carried out in an organic carboxylic acid. Organic carboxylic acids used for this method are preferred to be acetic acid, propionic acid, lactic acid or isolactic acid. These acids can be used in combination with higher acidic acid such as α-halogenated fatty acid or α-hydroxy fatty acid 8. the method being carried out in an inert organic solvent in the presence of an acidic substance.

Organic solvents used for this method are preferred to be saturated hydrocarbons such as hexane, heptane, cyclohexane, ethylcyclohexane, decaline, hexadecaline and squalane. Aromatic hydrocarbon, cyclic ether, ester, ketone, alcohol (especially tertiary alcohol) are preferred to be avoided at the conditions of the reaction, because these solvents could cause hydrogenation, ring-opening, hydrolysis, dehydration and the like, depending upon the reaction conditions. Acidic substances are preferred to be Bronsted acids such as sulfuric acid, hydrochloric acid, phosphoric acid, perchloric acid and boric acid; Lewis acids such as zinc chloride, and boron trifluoride; hydrogen salts of strong acid and strong base such as sodium hydrogen sulfate, sodium hydrogen phosphate and potassium hydrogen phosphate; salts of strong acid and strong base such as magnesium sulfate, zinc sulfate, calcium sulfate, copper sulfate, and magnesium chloride; solid acids such as silica alumina, alumina, and solid phosphoric acid; and organic acids such as acetic acid, formic acid, monochloroacetic acid and lactic acids.

Upon hydrogenolysis of the compounds (I) by the above method, combination of a catalyst with an acidic substance or combination of catalyst, with acidic substance and solvent is preferred to be such that the catalyst is not poisoned in part by acidic substance and/or solvent. The hydrogenolysis methods to be especially recommended from this reason and from the point of view of using industrially economic catalysts are as follows:

9. a method to be carried out in the presence of nickel or palladium catalyst supported on a carrier (for example, nickel catalyst supported on diatomaceous earth, palladium catalyst supported on active carbon and the like) or in the presence of a salt of strong acid and strong base or solid acid in the absence of a solvent or in an inert solvent; (10) a method to be carried out in the presence of a palladium catalyst supported on a carrier such as active carbon in an organic acid or in a mixture of an organic acid and an inert organic solvent being stable in the said organic acid.

The hydrogenolysis of the compounds (I) by means of the above methods is carried out in liquid phase at higher temperatures. The reaction temperature is preferred to be over about 100°C, especially at temperatures from 150° to 300°C. This reaction can be carried out at atmospheric pressure but it is preferred to be carried out at a high pressure of hydrogen and usually hydrogen pressures of about 10 – 100 kg/cm$^2$(G) are used. An amount of catalyst used varies with a kind of the catalyst, but it is generally in the broad range of about 0.1 – 10 %/w against the weight amount of the compound (I).

According to this invention, squalane can be prepared by means of another method. This method consists of two step reactions contrary to the above method. One step consists of mild partial hydrogenation of the compounds (I) resulting in the compounds having double bonds but no triple bonds that is, it consists of partial hydrogenation of only triple bonds contained in the compounds (I). Another step consists of hydrogenolysis of the above resultants resulting in squalane. That is, this step consists of replacing hydroxy radical or other radical as above mentioned with hydrogen and completing hydrogenation of the remaining unsaturated bonds contained in the above resultants and resulting in squalane.

The above method consisting of direct hydrogenolysis of the compounds (I) to squalane is liable to produce by-products considered to be skeleton isomers of squalane, because the compounds (I) are subject to rearrange under drastic conditions owing to triple bonds contained in the compounds (I). The byproducts are so difficult to separate from squalane that this method is defective in obtaining pure squalane. But the method consisting of two step reaction does not produce such by-products as above mentioned and can prepare purer squalane in a good yield.

With respect of partial hydrogenation, metal catalysts such as nickel, cobalt, palladium, platinum, rhodium, and iridium or their compounds or these catalysts supported on a suitable carrier may be used as hydrogenation catalysts. Especially, the catalysts which have strong hydrogenating activity and are preferred from the aspect of economy are Raney nickel, Raney cobalt or palladium on active carbon, barium sulfate or calcium carbonate. The hydrogen pressure in the reaction suffices to be below 100 kg/cm$^2$ and the hydrogenation may be carried out at atmospheric pressure. The hydrogenation reaction is preferred to be carried out in a suitable solvent because off high viscosity of the compounds (I). Any organic solvent of such a kind that does not hinder hydrogenation is used. These solvents are, for example, aliphatic hydrocarbons, aromatic hydrocarbons, ethers, esters, alcohols and organic carboxylic acids, but amines and compounds containing sulfur are not preferred. An amount of solvent used suffices to be at least the same amount of the compound (I) but it may be better below the same amount, provided the catalyst used is satisfactorily dispersed.

Thus squalane can be obtained by submitting the above partial hydrogenation products of the compounds (I) to hydrogeolysis. The conditions of this hydrogenolysis are almost the same as those of the above direct hydrogenation; therefore their details will be omitted for prevention of duplication but they will be obvious from the contents of the specification herein disclosed.

With respect to the preparation of squalane from the compounds (I), besides the methods according to this invention, a method comprising hydrogenation of the compounds (I), a dehydration and hydrogenation, or a method comprising transformation of the compounds (I) to saturated diol compounds, and hydrogenolysis can be considered; but according to the present inventors' experiments, squalane can be prepared in a better yield by the methods of this invention.

The following examples are given to further illustrate the present invention. The scope of the invention is not, however, meant to be limited to the specific details of the examples.

EXAMPLE 1

In a 5-l. three-necked, and round-bottomed flask were placed 114.7 g of 3,7,11-trimethyldodeca-6,10-dien-1-in-3-ol, 305.9 g of ammonium chloride, 765 ml of water and 76.5 ml of ethyl alcohol and the mixture was stirred at a room temperature by passing oxygen for 18 hours. After completion of the reaction, no starting material remained. The reaction mixture was centrifuged and was extracted with benzene. The organic layer was distilled off to remove benzene and ethyl alcohol. The residue was dissolved in benzene and washed with water. The benzene solution was dried over anhydrous calcium sulfate and the solid material was filtered off. The benzene solution thus obtained was distilled off to give 107.8 g of 2,6,10,15,19,23-hexamethyltetracosa-2,6,18,22-tetraene-11,13-diin-10,15-diol as viscous liquid. This substance was further dissolved in 10 ml of benzene, treated with active carbon and purified by distilling the benzene.

Elementary analysis for $C_{30}H_{46}O_2$ (%) Calculated: C; 82.14, H; 10.57, O; 7.29. Found: C; 81.86, H; 10.33, O; 7.58.

That this compound is 2,6,10,15,19,23-hexamethyltetracosa-2,6,18,22-tetraene-11,13-diin-10,15-diol was identified by means of the following method:

In 20 ml of acetic acid was dissolved 2 g of this compound and 0.2 ml of 3N-HCl, and 0.2 g of 5 % palladium on active carbon were added thereto. The mixture was hydrogenated at a hydrogen atmosphere of atmospheric pressure for 18 hours. Gas chromatography, NMR spectra and mass spectra of the main product showed that it is identical with available squalane. The theoretical amount of the hydrogen absorption was 1021 ml but its amount found was 1040 ml.

EXAMPLE 2

In a 1-l. three-necked and round-bottomed flask were placed 10.5 g of 3,7,11-trimethyldodeca-1-in-3-ol, 5.0 g of ammonium chloride, 12.0 g of tetramethylethylenediamine and 675 ml of pyridine. The mixture was reacted at temperatures of 50° - 55°C for 6 hours under an oxygen atmosphere. After completion of the reaction, the alcohol as a starting material was not detected. After distillation of pyridine from the reaction mixture, 300 ml of benzene and 200 ml of water were added to the residue and after decantation, the organic layer was washed with $3N-H_2SO_4$ and then water and dried. The benzene solution was distilled off to give 8.55 g of 2,6,10,15,19,23-hexamethyltetracosa-11,13-diin-10,15-diol as viscous liquid. This compound was treated with active carbon and purified in the same manner as in example 1.

Elementary analysis for $C_{30}H_{54}O_2$ of this purified compound (%) Calculated: C; 80.65, H; 12.18, O; 7.16. Found: C; 80.46, H; 12.05, O; 7.21.

That this compound is the object compound was identified by the fact that the mass analysis of this compound showed $M^+$ being 446 and that this compound gave squalane upon hydrogenolysis in the same manner as in example 1.

EXAMPLE 3

This example was worked out in the same manner as in example 2 except that 10.1 g of 3,7,11-trimethyldodeca-6,11-dien-1-in-3-ol was used in place of 3,7,11-trimethyldodeca-1-in-3-ol and 8.34 g of 2,6,10,15,19,23-hexamethyltetracosa-1,6,18,23-tetraene-11,13-diin-10,15-diol was thus obtained.

Elementary analysis for $C_{30}H_{46}O_2$ (%) Calculated: C; 82.14, H; 10.57, O; 7.29. Found: C; 82.04, H; 10,35, O; 7.59.

That this compound is the object compound was identified by the fact that it gave squalane on hydrogenolysis in the same manner as in example 1.

EXAMPLE 4

In a 2-l. three-necked and round-bottomed flask were placed 220 g of 3,7,11-trimethyl-6,10-dien-1-in-3-ol, 1 g of copper acetate, 20.2 ml of pyridine and 440 ml of n-heptane. The mixture was stirred at temperatures of 60°~70°C for 5 hours by passing oxygen. The reaction mixture was washed with a $3N-H_2SO_4$ -solution and then with a 10 % aqueous sodium chloride solution respectively three times and the n-heptane was distilled off to give 348 g of a crude product. A 100 g portion of this crude product was placed in a 500 ml autoclave and 200 ml of n-heptane, 1.8 g of nickel catalyst supported on diatomaceous earth which is roughly the same amount as that of nickel and 3.6 g of silica-alumina (alumina: 28~30 %) were added thereto. The mixture was subjected to hydrogenolysis at a temperature of 200°C under a hydrogen pressure of 100~20 kg/cm² with stirring for 16 hours. After filtering off the catalyst and distilling off the n-heptane, the residue was distilled off at 202° - 208°C under reduced pressure of 0.3 - 0.4 mmHg to give 45.0 g of squalane.

EXAMPLE 5

In a 500-ml autoclave 40 g of 6,10-dimethylundecan-2-one, 30 g of a 10 % solution of diacetylene in N-methylpyrrolidone and 200 ml of liquid ammonia were placed and the mixture was reacted at 20°C for 1 hour. After purging out ammonia, 200 ml of n-heptane was added to the residue and the mixture was washed with water and a crude product was obtained by distilling off the n-heptane. That the main components of the crude product are 6,10-dimethylundeca-2-one of the starting material and 2,6,10,15,19,23-hexamethyltetracosa-11,13-diin-10,15-diol obtained by example 2 was identified by means of gel parmeation chromatography (for the compounds of low molecular weight).

The crude product obtained by the above ethynylation was placed in a 300 ml shaking type Hastelloy autoclave (Hastelloy is the trade name of nickel alloy manufactured by Haynes Stellite Co.) and further 100 ml of acetic acid, and 0.6 g of 5 % Palladium on active carbon were added thereto. The mixture was shaken at 200°C under a hydrogen pressure of 100 ~ 50 kg/cm² for 16 hours. Gas chromatography showed that this reaction mixture contained 19.4 g of squalane.

EXAMPLE 6

In a 300-ml shaking type Hastelloy autoclave 20.0 g of 2,6,10,15,19,23-hexamethyltetracosa-2,6,18,22-tetraene-11,13-diin-10,15-diol obtained by the same method as in example 1, 40 ml of benzene and 1.0 g of 5 % palladium on carbon were placed and the mixture was subjected to hydrogenolysis at 200°C under a hydrogen pressure of 100 kg/cm$^2$ for 16 hours. Gas chromatography and NMR analysis showed that there remained no compound having unsaturated bonds and hydroxy radicals and the starting material was almost transformed into squalane.

EXAMPLE 7

In a 500 ml shaking type glass autoclave 10.0 g of 2,6,10,15,19,23-hexamethyltetracosa-2,6,18,22-tetraene-11,13-diin-10,15-diol obtained in the same manner as in example 1, 100 ml of acetic acid and 1.0 g of 5 % palladium on active carbon were placed and the mixture was subjected to hydrogenolysis at 150°C under a hydrogen pressure of 5 kg/cm$^2$ for 16 hours. An analysis of the crude product thus obtained showed that there remained no unsaturated compound and the main components consist of squalane and 2,6,10,15,19,23-hexamethyltetracosan-10-ol besides lower boiling substances and the area ratio of the former to the latter is 93:7 by means of gas chromatography.

EXAMPLE 8

In a 2-l. autoclave 1 l of liquid ammonia and 7 g of lithium were placed and 25 g of diacetylene was added thereto. To this solution 192 g of pseudoionone was added dropwise and reacted at 15°C for 5 hours. After completion of the reaction, the reaction mixture was cooled and neutralized by adding ammonium chloride. After purging liquid ammonia, the residue was dissolved in 1 l of n-hexane and 1 l of water. After decantation, the organic layer was washed with water several times and then the n-hexane was distilled off to give 200 g of the crude product.

A 100 g portion of the crude product, 100 ml of acetic acid and 1.0 g of 5 % palladium on active carbon were placed in a 500-ml shaking type glass autoclave. The mixture was subjected to hydrogenolysis at 150°C under a hydrogen pressure of 5 kg/cm$^2$ for 16 hours. An analysis of the crude product showed that there remained no unsaturated compound and the crude product consists of mainly squalane and 2,6,10,15,19,23-hexamethyltetracosan-10-ol.

EXAMPLE 9

In a 3-l round-bottomed flask was placed about 2 l of liquid ammonia and by adding 7 g of lithium and then passing acetylene gas thereto, lithium acetylide was prepared. To this solution 192 g of pseudoionone was added and the reaction mixture was subjected to reaction under reflux of ammonia for 8 hours by passing a little amount of acetylene. After completion of the reaction, ammonium chloride was added to neutrize the reaction mixture and after purging the liquid ammonia, the residue was dissolved in 1 l of n-hexane and 1 l of water and decanted. The organic layer obtained was washed with water several times and the n-hexane was distilled off to give 265 g of a crude product. The crude product was subjected to oxydative coupling reaction to give 426 g of a crude product in the same manner as in example 4 except that the crude product was used in place of 3,7,11-trimethyldodeca-6,10-dien-1-in-3-ol.

The crude product thus obtained was subjected to hydrogenolysis in the same manner as in example 8 to give a mixture of squalane and 2,6,10,15,19,23-hexamethyltetracosan-10-ol.

EXAMPLE 10

The ethynylation of 194 g of citronellidene acetone with diacetylene was worked out in the same manner as in example 8 except that citronellidene acetone was used in place of pseudoionone and 268 g of a crude product was thus obtained.

In a 500-ml shaking type glass autoclave a 10 g portion of the crude product, 100 ml of acetic acid and 1.0 g of 5 % palladium on active carbon were placed and the mixture was subjected to reaction at 150°C under a hydrogen pressure of 5 kg/cm$^2$ for 16 hours. An analysis of the crude product obtained showed there remained no unsaturated compounds and the crude product consists of mainly squalane and 2,6,10,15,19,23-hexamethyltetracosan-10-ol besides lower boiling compounds.

EXAMPLE 11

The ethynylation of 194 g of citronelliden acetone with acetylene was worked out in the same manner as in example 9 except that citronellidene acetone was used in place of pseudoionone and 278 g of a crude product was obtained. This product was subjected to oxydative coupling and hydrogenolysis in the same manner as in example 9 and squalane was thus obtained.

EXAMPLE 12

The ethynylation of 212 g of 6,10-dimethylundeca-3-en-2-on-10-ol obtained by aldol condensation of hydroxycitronellal and acetone with acetylene was worked out in the same manner as in example 9 except that hydroxycitronellal was used in place of pseudoionone and 269 g of a crude product was thus obtained.

The crude product was subjected to oxydative coupling in the same way as in example 4 except that it was used in place of 3,7,11-trimethyldodeca-6,10-dien-1-in-3-ol and 442 g of a crude product was thus obtained.

In a 300 ml autoclave 20 g of this crude product, 0.2 g of nickel on diatomaceous earth (nickel content: about 50 %), 0.4 g of silica-alumina catalyst and 80 ml of n-heptane were placed and the mixture was subjected to reaction at 230°C under a hydrogen pressure of 80 ~100 kg/cm$^2$ for 16 hours to give squalane.

EXAMPLE 13

In a 1-l three-necked and round-bottomed flask 10.1 g of 3,7,11-trimethyldodeca-6,11-dien-1-in-3-ol, 5.0 g of cuprous chloride, 12.0 g of tetramethylethylenediamine and 675 ml of pyridine were placed and the mixture was subjected to reaction at temperatures of 50° ~ 55°C under an oxygen atmosphere for 6 hours. After completion of the reaction there remained no starting alcohol. The pyridine was distilled off from the reaction mixture and the residue was dissolved in 300 ml of benzene and 200 ml of water and after decantation the organic layer was washed with a solution of 3N-H$_2$SO$_4$ and then with water and dried. The benzene solution was distilled off to give 8.34 g of 2,6,10,15,19,23-hexamethyltetracosa-1,6,18,23-tetraene-11,13-diin-10,15-diol. This product was purified with active carbon treatment and analyzed.

Elementary analysis for $C_{30}H_{46}O_2$ (%) Calculated: C; 82.14, H; 10.57, O; 7.29. Found: C; 82.04, H; 10.35, O; 7.59.

EXAMPLE 14

In a 2-l three-necked and round-bottomed flask 220 g of 3,7,11-trimethyldodeca-6,11-dien-1-in-3-ol, 9.1 g of copper acetate, 20.2 ml of pyridine and 440 ml of n-heptane were placed and the mixture was subjected to reaction at temperatures of 60°~70°C for 5 hours by passing oxygen and was washed with a $3N-H_2SO_4$ solution and with a 10 % aqueous solution of sodium chloride respectively three times. The n-heptane was distilled off to give 348 g of a crude product.

In a 300-ml autoclave a 100 g portion of this crude product, 3.6 ml of Raney nickel (about 2.5 g) and 100 ml of n-heptane were placed and the mixture was hydrogenated at room temperatures under a hydrogen pressure of 100 ~50 kg/cm² for 16 hours. The reaction temperature rose to a maximum temperature of about 55°C owing to heat of reaction. After the reaction, the Raney nickel was filtered off and the n-heptane was distilled off from the mixture to give 70.8 g of viscous brown liquid. Investigation with $C^{13}$-NMR spectra confirmed qualtitatively that this liquid has no triple bond and that some parts of the double bonds were hydrogenated, but a considerable amount of the double bonds remained.

This liquid was dissolved in 100 ml of isolactic acid and 1.5 g of 5 % palladium on active carbon was added thereto. This solution was placed in a 300-ml Hastelloy autoclave and caused to react at 200°C under a hydrogen pressure of 100 ~50 kg/cm² for 16 hours. The catalyst was filtered off and the reaction mixture was distilled under reduced pressure to give 33 g of squalane.

A 100 g portion of the above oxydative coupling product was caused to react in 100 ml of acetic acid in the same manner as above mentioned and 41.2 g of squalane was obtained by distillation. Investigation by gas chromatography (column: Diasolid M-2 % Carbowax 20 M 2 cm; temperature of measurement: 240°C) of this squalane showed that there is a substance having a sharp shoulder peak next to that of squalane. The structure of the substance showing this peak is not clear but that this substance is a saturated hydrocarbon is concluded by means of measurement of iodine number, infrared spectra and $C^{13}$-NMR spectra of this compound and therefore this substance seems to be a by-product which has a cyclized structure of squalane.

The above mentioned product in which the triple bonds were in advance removed by partial hydrogenation has not such a shoulder peak.

EXAMPLE 15

In a 200-ml autoclave 40 g of 6,10-dimethylundeca-5,10-dien-2-on, 30 g of a 10 % diacetylene solution in N-methylpyrrolidone, 1.5 g of potassium hydroxide and 200 ml of liquid ammonia were placed and the reaction was caused to react at 20°C for one hour. After removal of ammonia by purging, 200 ml of n-heptane was added to the residue and washed with water. The n-heptane was distilled off to afford a crude product. That the principal components of the crude product are 6,10-dimethylundeca-5,10-dien-2-on of the starting material and 2,6,10,15,19,23-hexamethyltetracosa-1,6,18,23-tetraene-11,13-diin-10,15-diol obtained by example 13 was confirmed by means of gel permeation chromatography (Column for low-molecular compounds). The crude product obtained by the above ethynylation was placed in a 300-ml shaking type autoclave and 40 ml of n-heptane and 0.8 g of 5 % palladium on active carbon were added thereto. The mixture was caused to react at temperatures from room temperature to 60°C under a hydrogen pressure of 50 ~100 kg/cm² for 16 hours. The crude product obtained had no triple bond but some double bonds. By adding further 20 ml of acetic acid to the above reaction system, the mixture was caused to react at 200°C under a hydrogen pressure of 50 ~100 kg/cm² for 10 hours. That 20.5 g of squalane having no shoulder peak as described in example 14 was obtained was confirmed by means of gas chromatography.

EXAMPLE 16

In a 500-ml autoclave 13.2 g of 2,6,10,15,19,23,-hexamethyltetracosa-2,6,18,22-tetraen-11,13-diin-10,15-diol obtained in the same manner as in example 1, about 0.65 g of 5 % palladium on active carbon, 100 ml of benzene were placed and the mixture was caused to react at 50°C at a hydrogen pressure of 4 ~6 kg/cm² for 6 hours. The catalyst was filtered out and the benzene was distilled off. That the crude product obtained had no triple bond but some double bonds was confirmed. To this crude product 100 ml of n-heptane, 0.40 g of nickel on the same amount of diatomaceous earth as that of nickel and 0.80 g of silica-alumina catalyst (alumina: 28 ~30 %) were placed and the mixture was caused to react at 220°C under a hydrogen pressure of 50 ~100 kg/cm² for 2 hours. Investigation by means of gas chromatography showed that there was obtained 11.0 g of squalane. The squalane had no shoulder peak as described in example 14.

EXAMPLE 17

In a 500 ml-autoclave 87.8 g of 2,6,10,15,19,23-hexamethyltetracosa-2,6,18,22-tetraene-11,13-diin-10,15-diol obtained in the same manner as in example 1, 2.6 g of Raney nickel and 200 ml of n-heptane were placed. The mixture was caused to react at temperatures from room temperature to 60°C under a hydrogen pressure of 50 - 100 kg/cm² for 3 hours. After removal of the catalyst, the n-heptane was distilled off to afford 10.4 g of a crude product having double bond but no triple bond.

To a 100-ml autoclave 10.2 g of the crude product, 40 ml of n-heptane, 0.2 g of nickel on diatomaceous earth and 1.0 g of zinc sulfate were placed. The mixture was caused to react at 200°C at a hydrogen pressure of 90 –1.00 kg/cm² for 16 hours to afford 2.3 g of squalane.

EXAMPLE 18

This example was worked out in the same manner as in example 17 except that 1.0 g of calcined gypsum was used in place of zinc sulfate and 7.4 g of squalane was obtained.

EXAMPLE 19

In a 2-l. autoclave 1 l of liquid ammonia, 17 g of lithium and 25 g of diacetylene were placed. To this solution 192 g of pseudoionone was added dropwise with stirring and caused to react at 15°C for 5 hours.

After completion of the reaction, the mixture was cooled and neutralized by adding ammonium chloride. After purging ammonia, the residue was dissolved in 1 l of n-hexane and 1 l of water. After decantation the organic layer was washed with water several times and the hexane was distilled off to afford 200 g of crude product.

In a 300-ml autoclave 100 g portion of the crude product, 3.6 ml of Raney nickel (about 2.5 g) and 100 ml of n-heptane were placed. The mixture was caused to react at a room temperature under a hydrogen pressure of 50 ~ 100 kg/cm². The reaction temperature in the reaction system rose to a maximum temperature of about 58°C owing to heat of reaction. After shaking for 16 hours, the Raney nickel was filtered off and the heptane was distilled off from the mixture to afford 108 g of crude product having no triple bond.

In a 100-ml autoclave 10.2 g of the above crude product, 40 ml of n-heptane, 0.2 g of nickel on diatomaceous earth, and 1.0 g of zinc sulfate were placed and the mixture was caused to react 200°C at a hydrogen pressure of 80 – 90 kg/cm² for 16 hours and 2.5 g of squalane (2,6,10,15,19,23-hexamethyltetracosane) was thus obtained.

EXAMPLE 20

In a 3-l round-bottomed flask was placed about 2l of liquid ammonia and by passing acetylene thereto after addition of lithium, lithium acetylide was prepared. After addition of 192 g of pseudoionone, this solution was caused to react under reflux of liquid ammonia for 8 hours by passing a little amount of acetylene. After the reaction, the solution was neutralized by adding ammonium chloride and after purging ammonia, the residue was dissolved in 1 l of n-hexane and 1 l of water. After decantation, the organic layer was washed with water several times and 265 g of a crude product was thus obtained.

The crude product was subjected to oxidative-coupling in the same manner as in example 14 except that it was used in place of 3,7,11-trimethyldodeca-6,10-dien-1-in-3-ol and 426 g of a crude product was thus obtained. A 100 g portion of the product was placed in a 500 ml autoclave and subjected to hydrogenation and hydrogenolysis in the same manner as in example 14 to give 21 g of squalane.

EXAMPLE 21

Ethynylation of 194 g of citronellidene acetone with diacetylene was operated in the same mannr as in example 19 except that citronellidene acetone was used in place of pseudoionone and 268 g of a crude product was thus obtained.

In a 300 ml autoclave 100 g of the crude product, 3.6 ml (about 2.5 g) of Raney nickel and 100 ml of n-heptane were placed and the mixture was caused to react at a room temperature under a hydrogen pressure of 50 ~ 100 kg/cm². The reaction temperature rose up to a maximum temperature of about 56°C. After shaking for 18 hours, the Raney nickel was filtered off and the heptane was distilled off to afford 112 g of a crude product having double bonds but no triple bond.

In a 100-ml autoclave 10.2 g of the crude product, 40 ml of n-heptane, 0.2 g of nickel on diatomaceous earth and 1.0 g of zinc sulfate were placed and the mixture was caused to react at 200°C under a hydrogen pressure of 80 – 90 kg/cm² for 10 hours to give 3.2 g of squalane (2,6,10,15,19,23-hexamethyltetracosane).

EXAMPLE 22

Ethynylation of 194 g of citronelliodene acetone was carried out with acetylene in the same manner as in example 20 except that citronellidene acetone was used in place of pseudoionone and 278 g of a crude product was thus obtained. This product was subjected to oxydative-coupling, hydrogenation and hydrogenolysis in sequence in the same manner as in example 20 and squalane was thus obtained in a yield of 36.3 % from citronellidene acetone to squalane.

EXAMPLE 23

Ethynylation of 212 g of 6,10-dimethylundeca-3-en-2-on-10-ol obtained by aldol condensation of hydroxycitronellal and acetone was carried out in the same manner as in example 20 except that hydroxycitronellal was used in place of pseudoionone and 269 g of a crude product was thus obtained.

The crude product was subjected to oxydative-coupling reaction in the same manner as in example 14 except that it was used in place of 3,7,11-trimethyldodeca-6,10-dien-1-in-3-ol and 442 g of a crude product was thus obtained.

In a 300 ml round-bottomed flask a 50 g portion of the product, 50 ml of n-heptane and 5 g of 5 % Lindlar catalyst were placed and the mixture was caused to react at 50°C under normal atmospheric pressure for 8 hours. That the product thus obtained had almost no triple bond but only double bonds was confirmed by means of its $C^{13}$-NMR spectra. After filtering off the Lindlar catalyst, the product was placed in a 300-ml autoclave and the hydrogenolysis catalysts used in example 16, 1.5 g of nickel on diatomaceous earth and 3 g of silica-alumina catalyst, were added thereto. The mixture was caused to react at 230°C under a hydrogen pressure of 80 ~ 100 kg/cm² for 5 hours. That the product thus obtained contained 14.2 g of squalane was confirmed by means of gas chromatography.

What is claimed is:

1. A compound having the general formula

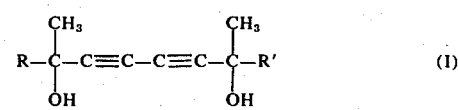

wherein R and R' are the same or different and represent saturated or unsaturated hydrocarbon residues having 11 carbon atoms represented by the following carbon atom skeleton:

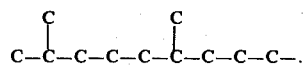

2. A compound of formula (I) as claimed in claim 1 selected from the group consisting of the following compounds:

2,6,10,15,19,23-hexamethyltetracosa-2,6,18,22-tetraene-11,13-diin-10,15-diol,
2,6,10,15,19,23-hexamethyltetracosa-18,22-diene-11,13-diin-10,15-diol,
2,6,10,15,19,23-hexamethyltetracosa-1,6,18,22-tetraene-11,13-diin-10,15-diol,
2,6,10,15,19,23-hexamethyltetracosa-2,6,8,18,22-pentaene-11,13-diin-10,15-diol, 2,6,10,15,19,23-hexamethyltetracosa-2,8,18,22-tetraene-11,13-diin-10,15-diol,
2,6,10,15,19,23-hexamethyltetracosa-8,18,22-triene-11,12-diin-10,15-diol,
2,6,10,15,19,23-hexamethyltetracosa-11,13-diin-10,15-diol,
2,6,10,15,19,23-hexamethyltetracosa-1,6-diene-11,13-diin-10,15-diol,
2,6,10,15,19,23-hexamethyltetracosa-2,6,8-triene-11,13-diin-10,15-diol,
2,6,10,15,19,23-hexamethyltetracosa-2,8-diene-11,13-diin-10,15-diol,
2,6,10,15,19,23-hexamethyltetracosa-8-ene-11,13-diin-10,15-diol,
2,6,10,15,19,23-hexamethyltetracosa-1,6,18,23-tetraene-11,13-diin-10,15-diol,
2,6,10,15,19,23-hexamethyltetracosa-2,6,8,18,23-pentaene-11,13-diin-10,15-diol,
2,6,10,15,19,23-hexamethyltetracosa-2,8,18,23-tetraene-11,13-diin-10,15-diol,
2,6,10,15,19,23-hexamethyltetracosa-8,18,23-triene-11,13-diin-10,15-diol,
2,6,10,15,19,23-hexamethyltetracosa-2,6,8,16,18,22-hexaene-11,13-diin-10,15-diol,
2,6,10,15,19,23-hexamethyltetracosa-2,8,16,18,22-pentaene-11,13-diin-10,15-diol,
2,6,10,15,19,23-hexamethyltetracosa-8,16,18,22-tetraene-11,13-diin-10,15-diol,
2,6,10,15,19,23-hexamethyltetracosa-2,8,16,22-tetraene-11,13-diin-10,15-diol,
2,6,10,15,19,23-hexamethyltetracosa-8,16,22-triene-11,13-diin-10,15-diol and
2,6,10,15,19,23-hexamethyltetracosa-8,16-diene-11,13-diin-10,15-diol.

3. 2,6,10,15,19,23-Hexamethyltetracosa-2,6,18,22-tetraene-11,13-diin-10,15-diol of claim 1.

4. 2,6,10,15,19,23-Hexamethyltetracosa-18,22-diene-11,13-diin-10,15-diol of claim 1.

5. 2,6,10,15,19,23-Hexamethyltetracosa-11,13-diin-10,15-diol of claim 1.

6. 2,6,10,15,19,23-Hexamethyltetracosa-1,6,18,23-tetraene-11,13-diin-10,15-diol of claim 1.

* * * * *

UNITED STATES PATENT OFFICE
CERTIFICATE OF CORRECTION

PATENT NO. : 3,981,930

DATED : September 21, 1976

INVENTOR(S) : TAKASHI NISHIDA et al

It is certified that error appears in the above-identified patent and that said Letters Patent are hereby corrected as shown below:

Column 1, line 34: replace "$C_{15}$-ketone" with --- $C_{13}$-ketone ---.

Column 1, lines 37-40, Fig. (II): replace "$R'-\underset{O}{\overset{|}{C}}-CH_3$"

with --- $R'-\underset{O}{\overset{\|}{C}}-CH_3$ ---.

Column 2, line 19: replace "squalane" with --- squalene ---.

Column 2, lines 61-64, Fig. (II): replace "$R'-\underset{O}{\overset{|}{C}}-CH_3$"

with --- $R'-\underset{O}{\overset{\|}{C}}-CH_3$ ---.

Column 4, line 67: replace "2,8,16,18-pentaene" with --- 2,8,16,18,22-pentaene ---.

UNITED STATES PATENT OFFICE
CERTIFICATE OF CORRECTION

Patent No. 3,981,930   Dated September 21, 1976

Inventor(s) Takashi Nishida et al.

It is certified that error appears in the above-identified patent and that said Letters Patent are hereby corrected as shown below:

Column 5, line 1, "8,18,22-tetraene" should read
-- 8,16,18,22-tetraene --.

Signed and Sealed this

Thirty-first Day of May 1977

[SEAL]

Attest:

RUTH C. MASON
Attesting Officer

C. MARSHALL DANN
Commissioner of Patents and Trademarks